United States Patent
Corn et al.

(10) Patent No.: US 7,670,556 B2
(45) Date of Patent: Mar. 2, 2010

(54) SURFACE PLASMON RESONANCE IMAGING OF MICRO-ARRAYS

(75) Inventors: Robert M. Corn, Madison, WI (US); Hye Jin Lee, Madison, WI (US); Terry T. Goodrich, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1229 days.

(21) Appl. No.: 10/192,026

(22) Filed: Jul. 10, 2002

(65) Prior Publication Data

US 2003/0017579 A1 Jan. 23, 2003

Related U.S. Application Data

(60) Provisional application No. 60/304,246, filed on Jul. 10, 2001.

(51) Int. Cl.
*G01N 33/50* (2006.01)
*G01N 13/00* (2006.01)

(52) U.S. Cl. .................... 422/68.1; 422/50; 422/55; 506/7; 506/39

(58) Field of Classification Search .............. 435/4, 435/6, 7.1, 283.1, 287.1, 287.2, 287.9, 288.4, 435/288.5
See application file for complete search history.

(56) References Cited

U.S. PATENT DOCUMENTS

| | | | |
|---|---|---|---|
| 5,374,563 A * | 12/1994 | Maule | 436/165 |
| 5,545,531 A * | 8/1996 | Rava et al. | 435/6 |
| 5,629,213 A | 5/1997 | Kornguth et al. | |
| 5,677,195 A * | 10/1997 | Winkler et al. | 436/518 |
| 5,929,208 A | 7/1999 | Heller et al. | |
| 5,942,443 A * | 8/1999 | Parce et al. | 436/514 |
| 6,040,193 A | 3/2000 | Winkler et al. | |
| 6,127,129 A | 10/2000 | Corn et al. | |
| 6,139,831 A | 10/2000 | Shivashankar et al. | |
| 6,576,478 B1 * | 6/2003 | Wagner et al. | 436/518 |

OTHER PUBLICATIONS

Waseda et al., "Surface Plasmon Resonance Detector for Capillary Chip Electrophoresis", 1999, Chemistry Letters, vol. 28, No. 11, pp. 1195-1196.*

(Continued)

*Primary Examiner*—Christopher Low
*Assistant Examiner*—Christopher M. Gross
(74) *Attorney, Agent, or Firm*—Joseph T. Leone, Esq.; DeWitt Ross & Stevens

(57) ABSTRACT

Disclosed is a method for fabricating 1-dimensional micro-arrays using parallel micro-fluidic channels on chemically-modified metal, carbon, silicon, and/or germanium surfaces; a μL detection volume method that uses 2-dimensional nucleic acid micro-arrays formed by employing the 1-dimensional DNA micro-arrays in conjunction with a second set of parallel micro-fluidic channels for solution delivery, and the 1-dimensional and 2-dimensional arrays used in the methods. The methodology allows the rapid creation of 1- and 2-dimensional arrays for SPR imaging and fluorescence imaging of DNA-DNA, DNA-RNA, DNA-protein, and protein-protein binding events. The invention enables very small volumes necessary for a variety of bioassay applications to be analyzed by SPR. Target solution volumes as small as 200 pL can be analyzed.

10 Claims, 6 Drawing Sheets

(a)

(b) Cross-sectional view of the DNA microarray featuring a simplified SPR imaging experimental set up

OTHER PUBLICATIONS

Effenhauser et al., "Integrated Capillary Electrophoresis on Flexible Silicone Microdevices: Analysis of DNA Restriction Fragments and Detection of Single DNA Molecules on Microchips", Sep. 1, 1997, Analytical Chemistry, vol. 69, No. 17, pp. 3451-3457.*
Homola et al., "Novel approach to multichannel SPR sensing", Nov. 1999, Proceedings of SPIE, vol. 3857, pp. 198-206.*
O'Brien II et al., "A surface plasmon resonance array biosensor based on spectroscopic imaging", Jan. 2001, Biosensors and Bioelectronics, vol. 16, Issues 1-2, pp. 97-108.*
Science Direct database bibliography entry concerning O'Brien, II et al. (Biosensors & Bioelectronics, Jan. 2001, 16(1-2), pp. 97-108).*
Lofas and Johnsson (1990 J. Chem. Chem. Commun. 1526-1528).*
Delamarche et al (1998 JACS 120:500-508).*
Salamon et al (2001 Biophysical J 80:1557-1567).*
Anderson et al. (2000) *Anal. Chem.* 72:3158-3164.
Brockman et al. (1999) *J. Am. Chem. Soc.* 121:8044-8051.
Brockman et al. (2000) *Ann. Rev. Phys. Chem.* 51:41:63.
Duffy et al. (1998) *Anal. Chem.* 70:4974-4984.
Effenhauser et al. (1997) *Anal. Chem.* 69:3451-3457.
Fodor (1997) *Science* 277:393-395.
Frutos et al. (1997) *Nucleic Acids Res.* 25:4748-4757.
Frutos et al (1998) *J. Am. Chem. Soc.* 120:10277-10282.
Frutos et al. (1998) *Anal. Chem.* 70:449A-455A.
Frutos et al. (2000) *Langmuir* 16:2192-2197.
Hickel et al. (1989) *Nature* 339:186.
Jo et al. (2000) *Microelectrochemical Systems* 9:76-81.
Jordan et al. (1997) *Anal. Chem.* 69:4939-4947.
Jordan & Corn 1997 *Anal. Chem.* 69(7):1449-1456.
Lee et al., (2001) *Anal. Chem.* 73:5525-5531.
Liedberg et al. "Sensors and Actuators," vol. 4, 1983, p. 299.
Lockhart, et al. (1996) *Nature Biotechnology* 14:1675-1680.
Nelson et al. (1999) *Anal. Chem.* 71:3928-3934.
Nelson et al. (2001) *Anal. Chem.* 73:1-7.
Pease et al. (1994) *Proc. Natl. Acd. Sci. USA* 91:5022-5026.
Rothenhausler & Knoll (1988) *Nature* 332:615-617.
Silin & Plant (1997) *Trends in Biotechnol.* 15.
Strother et al. (2000a) *Nucleic Acids Research* 28:3535-3541.
Strother et al. (2000b) *J. Am. Chem. Soc.* 122:1205-1209.
Tarlov et al. (1993) *J. Am. Chem. Soc.* 115:5305-5306.
Thiel et al. (1997) *Anal. Chem.* 69:4948-4956.
Thomas et al. (1995) J Am. Chem. Soc. 117:3830-3834.
Winzeler et al. (1998) *Science* 281:1194-1197.

* cited by examiner

(b) Cross-sectional view of the DNA microarray featuring a simplified SPR imaging experimental set up

FIG. 3

(a) Target DNA A (b) Target DNA B (b) Target DNA C (d) Mixture of 3 DNA targets

SURFACE PLASMON RESONANCE IMAGING OF MICRO-ARRAYS

PRIORITY

Priority is hereby claimed to provisional application Ser. No. 60/304,246, filed Jul. 10, 2001, the entire contents of which is incorporated herein by reference.

FEDERAL FUNDING

This invention was made with United States government support awarded by the following agencies: NSF: 9820742. The United States has certain rights in this invention.

FIELD OF THE INVENTION

The invention is directed to a method of producing chemical micro-arrays (preferably nucleic acid micro-arrays) on chemically-modified gold and silicon films using micro-fluidics techniques, the micro-arrays produced thereby, and a method of analyzing the arrays using surface plasmon resonance (SPR) techniques. The SPR imaging techniques can, for example, be used to detect the affinity binding of unlabeled biological molecules onto arrays attached to the gold surface. The inventive techniques described herein provide simple, inexpensive, and powerful tools for the label-free detection of biomolecules.

INCORPORATION BY REFERENCE

All of the documents cited herein are incorporated by reference.

DESCRIPTION OF THE RELATED ART

The binding of proteins to DNA plays a pivotal role in the regulation and control of gene expression, replication and recombination. In addition, enzymes that recognize and modify specific oligonucleotide sequences are critical components of biological nucleic acid manipulation and repair systems. An enhanced understanding of how these proteins recognize certain oligonucleotide sequences would aid in the design of biomedical systems which could, for example, be used to regulate the expression of therapeutic proteins. For this reason, the study of protein-nucleic acid interactions (i.e., protein-DNA and protein-RNA interactions) is a rapidly growing area of molecular biology, aided in part by recent advances in NMR and X-ray structural determination methods. At the same time, the explosive increase in the amount of available genomic and extra-genomic (i.e., ribosomal) sequence information obtained from large-scale nucleic acid sequencing efforts creates a need to survey this vast amount of new sequence data for protein binding sites. The present invention addresses this need by using surface plasmon resonance (SPR) imaging techniques as a rapid and efficient method for screening the sequence or structure-specific binding of proteins, DNA, or RNA to large arrays of nucleic acid molecules immobilized at chemically-modified metal surfaces.

Arrays of DNA molecules attached to planar surfaces are currently employed in hybridization adsorption experiments to sequence DNA, Pease et al. (1994); to screen for genetic mutations, Winzeler et al. (1998): and in DNA computing applications, Frutos et al. (1997) and Frutos et al. (1998) (*J. Am. Chem. Soc.*). These arrays are exposed to solutions containing fluorescently labeled complementary DNA sequences, rinsed, and then "read-out" using fluorescence imaging methods.

The technique of surface plasmon resonance (SPR) is a surface-sensitive, optical detection method well suited to the monitoring of reversible, protein-nucleic acid interactions. The commercially successful "BIAcore" SPR instrument (Biacore AB, Uppsala, Sweden) has been used previously, for example, to study the interaction of DNA molecules with various enzymes. Although powerful, the "BIAcore" instrument has no imaging capabilities. This severely limits the number of DNA sequences that can be screened in a single experiment.

Surface plasmon resonance (SPR) is a surface optical technique which is sensitive to the thickness and index of refraction of material at the interface between a free electron metal (e.g., gold, silver, copper, cadmium, aluminum) and a bulk medium, such as air or water. Surface plasmon resonance may be achieved by using the evanescent wave which is generated when a laser beam linearly polarized parallel to the plane of incidence impinges onto a prism coated with a thin metal film. The metal may also be coated onto a thin transparent substrate such as glass, and this glass brought into optical contact with the prism. SPR is most easily observed as a reduction of the total internally reflected light just past the critical angle of the prism. This angle of minimum reflectivity (denoted as the SPR angle) shifts to higher angles as material is adsorbed onto the metal layer. The shift in the angle can be converted to a measure of the thickness of the adsorbed or added material by using complex Fresnel calculations and can be used to detect the presence or absence of materials on top of the metal layer.

In using SPR to test for biological, biochemical, or chemical substances, a beam of light from a laser source is directed through a prism onto a biosensor consisting of a transparent substrate, usually glass, which has one external surface covered with a thin film of a noble metal, which in turn is covered with an organic film that interacts strongly with an analyte, such as a biological, biochemical, or chemical substance. The organic film can contain substances, such as antibodies or antigens, which can bind with an analyte in a sample to cause an increased thickness which will shift the SPR angle. By monitoring either the position of the SPR angle or the reflectivity at a fixed angle near the SPR angle, the presence or absence of an analyte in the sample can be detected.

Various types of equipment for using SPR with a biosensor for biological or biochemical or chemical substances are described by the Liedberg et al. article found in "Sensors and Actuators," Vol. 4, 1983, page 299. See also European Patent Application 0 305 108 and U.S. Pat. No. 5,374,563.

The use of conventional SPR as a testing tool offers several advantages and disadvantages. For example, it is relatively fast, it requires no labeling, and it can be performed on site. However, as noted above, commercially-available devices, such as the "BIAcore" instrument, offer no imaging capabilities. Additionally, to achieve the high through-put demanded by large-scale users, there is a need for a simple, practical biosensor that can be readily modified or adapted to test a wide variety of compounds simultaneously.

In SPR imaging, a light source (typically a monochromatic, incoherent, near-infrared light source) is used to illuminate a prism/thin gold film sample assembly at an incident angle that is near the SPR angle, and the reflected light is detected at a fixed angle with a CCD camera to produce an SPR image. The SPR image arises from variations in the reflected light intensity from different parts of the sample; these variations are created by any changes in organic film thickness or index of refraction that occur upon adsorption of chemical species onto the modified gold surface. Because SPR imaging is sensitive only to molecules in close proximity to the surface (within~200 nm), unbound molecules remaining in solution do not interfere with in situ measurements.

The formation of robust, reproducible arrays of oligonucleotides tethered to metalcoated surfaces (most often gold) is an essential requirement for SPR imaging of proteinnucleic acid binding interactions. To use SPR imaging techniques, it is essential that the nucleic acid array be constructed on a noble metal surface, and for this reason DNA arrays on glass supports from commercially available sources such as Affymetrix (Santa Clara, Calif.) are not a viable option. Using self-assembled monolayers of substituted alkanethiols as a starting point, others have previously developed schemes to attach single-stranded DNA molecules to chemically-modified gold surfaces. See, for instance, U.S. Pat. No. 5,629,213). In the subject invention, however, micro-fluidic techniques are brought to bear to allow micro-arrays to be assembled in a site-directed manner on the metal surface, thereby enabling the creation of multi-component one-dimensional and two-dimensional arrays.

Nucleic acid array technology itself has revolutionized the practice of life sciences research, providing quantitative information on complex biological systems in a fraction of the time required by traditional methods. However, the application of such technology for quantitative measurement of biomolecules has been limited by the high costs and laborious techniques associated with radioactive and fluorescent labeling and detection (Lockhart et al. (1996); Fodor (1997)).

Micro-array technology was developed as a faster, easier, label-free detection method. However the current techniques remain impractical for large-scale screening of biomolecules, primarily because they require photo-patterning or reversible protection chemistry, which make these techniques time-consuming and often prohibitively expensive. Current micro-array techniques also require large amounts of chemicals in the fabrication process, and cannot detect the small volumes often used in molecular biology laboratories. Thus, there remains a need for a fast, simple, inexpensive, and reusable micro-array technology for large-scale screening of biomolecules. Additionally, current micro-arrays cannot be re-used multiple times, and thus require the researcher to devote a substantial amount of time simply to create the array substrates for each experiment.

SPR imaging is a surface optical technique that has been used extensively to measure the label-free binding of biological molecules onto chemically- and biologically-modified surfaces, Silin & Plant (1997). SPR imaging allows multiple molecular probes to be analyzed simultaneously for affinity to a target molecule or mixtures of target molecules. Brockman et al. (1999); Nelson et al. (2001). SPR imaging has been used for the analysis of DNA hybridization, Jordan et al. (1997); Thiel et al. (1997), the detection of RNA oligonucleotide hybridization, and DNA-protein interactions, Brockman et al. (1999); Brockman et al. (2000); Frutos et al. (2000).

SPR can be coupled with the use of near-infrared (NIR) excitation. This technique results in improved image contrast and better sensitivity over the more commonly used excitation from a beam-expanded visible laser, Nelson et al. (1999). An NIR-SPR imager device uses light from a collimated white light source to illuminate a high index glass prism at a fixed angle. A gold-coated glass slide containing a nucleic acid array is optically coupled to the prism. Using UV-photo patterning techniques, Tarlov et al. (1993), gold surfaces are chemically-modified to create spatial arrays of molecules for use with SPR imaging (see U.S. Pat. No. 6,127,129). Light at 800 nm interacts with the patterned thin film from behind, creating surface plasmons. Reflectivity of the incident light is attenuated upon the creation of the surface plasmons; the momentum of these surface plasmons is determined by the index of refraction very close to the gold film. Adsorption of molecules such as nucleic acids onto the surface affects the index of refraction very close to the surface, thereby causing a change in the reflectivity of incident light. These changes in reflectivity are monitored with a CCD camera.

Overall, the new technology described herein gives researchers (i) a means of high-through put screening; (ii) permits the detection of biomolecule interactions using SPR imaging measurements in very small volumes; and (iii) allows the simultaneous detection of multiple hybridization reactions during SPR experiments.

SUMMARY OF THE INVENTION

A first embodiment of the invention is directed to a method of fabricating a biomolecule micro-array on a chemically-modified substrate. This first embodiment of the invention comprises first, in face-to-face orientation, reversibly attaching a thin film having disposed therein one or more micro-grooves to a chemically-modified substrate, thereby defining one or more micro-channels. It is preferred that the thin film be made from PMDS. Then, one or more biomolecules is passed through the micro-channels such that the biomolecules bind to the surface of the chemically-modified substrate at points within the micro-channels. The thin film is then removed from the chemically-modified substrate, thereby yielding a chemically-modified substrate having deposited thereon an array of biomolecules.

A second embodiment of the invention is directed to a method of fabricating a micro-fluidic, biomolecule micro-array on a chemically-modified substrate. This second embodiment of the invention comprises the same steps recited in the previous paragraph, and then, after removing the thin film from the chemically-modified substrate, reversibly attaching (in face-to-face orientation) a second thin film having disposed therein one or more micro-grooves to the substrate in such a fashion that the micro-grooves of the second thin film intersect the array of biomolecules, thereby defining a distinct set of micro-channels through which can be passed reagents that will make contact with the array of biomolecules deposited on the substrate.

A third embodiment of the invention is directed to a micro-fluidic, biomolecule micro-array on a chemically-modified substrate comprising a chemically-modified substrate having defined thereon an array of biomolecules. A thin film having disposed therein one or more micro-grooves is reversibly attached in face-to-face orientation to the chemically-modified substrate in such a fashion that the micro-grooves of the thin film intersect the array of biomolecules, thereby defining a set of micro-channels through which can be passed reagents that will make contact with the array of biomolecules deposited on the substrate.

A fourth embodiment of the invention is drawn to a method of analyzing interactions between biomolecules. Here, the method comprises providing a micro-fluidic, biomolecule micro-array on a chemically-modified substrate as described in the immediately preceding paragraph. Then passing through the micro-channels one or more solutions suspected of containing molecules capable of interacting with the array of biomolecules bound to the chemically-modified substrate. The chemically-modified substrate is then analyzed to determine if any interaction has occurred. Preferably the analysis is performed by SPR or fluorescence microscopy.

In the present invention, a new technology is described for making micro-arrays using micro-fluidic channels. The technology places two or more micro-fluidic channels on a chemically-modified gold or silicon surface, combined with a detection methodology using another series of parallel micro-fluidic channels. This micro-array set-up then uses SPR imaging to detect unlabeled biomolecules. SPR imaging allows simultaneous analysis of multiple molecular probes for affinity against a target molecule. (Hickel et al. 1989; Rothenhausler & Knoll 1988; Brockman et al. 2000).

Disclosed is a method to fabricate micro-arrays on thin gold films by utilizing micro-fluidic channels, and then applying surface plasmon resonance imaging techniques to detect bio-molecules. This procedure draws on the previously described SPR imaging technique, which analyzes the affinity interactions of multiple molecular probes simultaneously. With SPR imaging, it is then possible to measure the binding of biological molecules onto chemically- or biologically-modified surfaces without the use of labels.

The benefits and uses of the invention are many. The devices and methods described herein are useful to analyze interactions between all types of biomolecules, including, but not limited to DNA-DNA interactions, DNA-RNA interactions, DNA/RNA-protein interactions and protein-protein interactions.

The methods to fabricate biomolecule arrays are also useful to fabricate such arrays very, very quickly, using a minimum amount of chemical reagents, and requiring only a minimal amount of training.

The primary benefits of the present methods and devices is that they allow SPR techniques to be utilized using only very small amounts of sample, as small as 200 pL, a volume significantly smaller than the roughly 500 μL amount required by conventional SPR techniques.

The arrays produced according to the present invention are also reusable. The substrates can be stripped clean using 8 M urea and new arrays fabricated on the old substrates. This saves time and money and resources.

BRIEF DESCRIPTION OF THE DRAWINGS

FIGS. 2A and 2B are SPR difference images showing hybridization of target DNA onto an array of surface-bound probe DNA. Hybridization onto the probe DNA array is indicated by a change in the percent reflectivity. FIG. 2A depicts a 1-dimensional micro-array composed of the same probe DNA sequence in all the channels; FIG. 2B depicts a 1-dimensional micro-array comprising multiple probes of differing sequence.

DETAILED DESCRIPTION OF THE INVENTION

Abbreviations and Commercial Suppliers

The following abbreviations and terms are used throughout the specification and claims. All other terms have their standard, accepted meaning in the relevant art.

"biomolecule"=any molecule found in biological material, expressly including, but not limited to, nucleic acids, proteins, peptides, antibodies, enzymes, cell-wall components such as phospholipids, etc., and modified and synthetic forms thereof, such as labeled biomolecules and recombinant biomolecules.

"BSA"=bovine serum albumin (Sigma Chemical, St. Louis, Mo.). "metal substrate" or "metal film" or "chemically-modified substrate"=a substrate, preferably of gold, silver, platinum, copper, cadmium, aluminum, silicon, germanium, and/or carbon. Gold is preferred. It is also preferred that the substrate be SPR-capable. Chemically-modified means that the substrate has adhered or chemically bonded to it one or more layers of chemical reagents that enable biomolecules and/or cells to be immobilized on the substrate. As used herein, these terms expressly include the chemically-modified substrates described in U.S. Pat. No. 6,127,129.

"MUAM"=11-mercaptoundecylamine (Dojindo Co., Kumamoto, Japan).

"NHSS"=N-hydroxysulfosuccinimide ester.

"nucleic acids"=deoxyribonucleic acids (DNA), ribonucleic acids (RNA), and peptide nucleic acids from any source, and modified forms thereof, including, without limitation, labeled (radioactive, fluorescent, etc.) nucleic acids, and nucleic acids modified to include a binding moiety such as a thiol group or a biotin tag.

"PDMS"=polydimethylsiloxane.

"PEG"=poly(ethylene glycol).

"PEG-NHS"=N-hydroxysuccinimidyl ester of methoxy-poly(ethylene glycol) propionic acid MW 2000 (Shearwater Polymers, Inc., Huntsville, Ala.).

"SPR"=surface plasmon resonance.

"SSB"=single-stranded DNA binding protein (Pharmacia Biotech, Piscataway, N.J.).

"SSMCC"=sulfosuccinimidyl 4-(N-maleimidomethyl)cyclohexane-1-carboxylate (Pierce Chemical, Rockford, Ill.).

"TAEA"=tris(2-aminoethyl)amine (Aldrich Chemical, Milwaukee, Wis.).

"TEA"=triethanolamine hydrochloride (Sigma)

"ω-modified alkanethiol"=an alkanethiol whose terminal carbon atom has been modified by the addition of a chemically-reactive moiety such as an amino, hydroxy, carboxy, or thiol moiety.

Overview

The instant invention provides (i) a method for fabricating 1-dimensional DNA micro-arrays using micro-fluidic channels on chemically-modified (preferably gold and silicon) surfaces; and (ii) a microliter-level detection volume methodology that uses 2-dimensional DNA micro-arrays formed by employing the 1-dimensional micro-arrays in conjunction with a second set of parallel micro-fluidic channels. These micro-channels are preferably made from polydimethylsiloxane (PDMS) polymer using a well-established, simple, rapid, and low cost fabrication methodology. The methodology is described in Anderson et al. (2000). See also Jo et al. (2000); Duff et al. (1998); and Effenhauser et al. (1997). These arrays can be used to detect the specific adsorption of DNA, RNA, and proteins with the techniques of fluorescence microscopy and surface plasmon resonance (SPR) imaging.

The method for creating 1-dimensional micro-arrays via micro-fluidics provides a simple strategy for creating arrays with a vast number of different probe molecules immobilized on one array surface. The number of different probes that can be immobilized on a single surface is limited only by the size of the surface and the size of each individual array element.

The method also has an advantage of being much simpler than the existing DNA micro-array fabrication techniques. These earlier techniques are based on photo patterning and reversible protection chemistry. This new methodology disclosed herein reduces the time required to make an array and also reduces the amount of chemicals required in the fabrication process.

The method draws on the technology that has been recently been used in SPR imaging experiments. SPR imaging is a surface sensitive optical technique that detects the affinity binding of unlabeled biological molecules onto arrays of molecules attached to chemically-modified gold surfaces that is emerging as a powerful tool for the label-free detection of biomolecules in a high density array format. Using SPR imaging, measurements can easily be made of DNA micro-arrays fabricated on gold surfaces, and can be used to monitor DNA-DNA, RNA-DNA, or protein-DNA interactions down to nanomolar concentrations. By mating micro-fluidics to the SPR imaging experiment, the volume of test solution required can be reduced from 500 μL to 200 pL, allowing the use of femtomole amounts of DNA or RNA. This method provides a simple way to place tens to thousands (even tens of thousands) or more of different probes on one array for detecting binding events from biological samples (DNA, RNA, proteins, etc.) with SPR imaging and/or fluorescence microscopy.

Creating Microfluidic Channels

The preferred methodology used herein to fabricate microfluidic channels is to create the required channels in etched PDMS. In the preferred embodiment, the PDMS-defined microfluidic channels were created following the approach described in Anderson et al. (2000). Specifically designs for the desired channel systems are generated using a CAD program (or other suitable design program), such as Macromedia's Freehand (Macromedia, San Francisco, Calif.). High-resolution transparencies are then produced from the CAD file using a high-resolution laser printer or via even higher resolution off-set printing (available at any commercial print shop or service bureau). A negative photoresist, such as SU 8-50 (Microlithography Chemical Corp., Newton, Mass.), is then spin-coated onto a silicon wafer and soft-baked to drive off solvent. The transparency is then used as a photomask and the photoresist is exposed (~ 45 sec) to yield features approximately 50 μm high. As described in Anderson et al., the process can be repeated any number of times to yield microchannels of considerable complexity, in virtually any geometry.

After exposure, the silicon wafer is hard-baked (~ 5 min). The silicon wafer is then developed in propylene glycol methyl ether acetate and silanized in vacuo with a small amount (several drops) of tridecafluoro-1,1,2,2-tetrahydrooctyl-1-trichlorosilane (United Chemical Technologies, Inc., Bristol, Pa.). Silanizing the master silicon wafer facilitates removal of the PDMS replica after molding.

To make the mold or housing that will define at least part of the walls of the microfluidic channels, the developed and baked silicon wafer is covered with a PDMS prepolymer and cured at 75° C. for one hour. The cured PDMS polymer is then very gently peeled from the silicon wafer, trimmed, oxidized in a plasma cleaner, and silanized using tridecafluoro-1,1,2,2-tetrahydrocotyl-1-trichlorosilane.

The PDMS mold or housing can then be attached, in face to face orientation, to a modified, preferably SPR-capable, substrate, thereby defining one or more micro-channels wherein the chemically-modified substrate forms at least one wall defining the channel itself. Various chemicals can then be flowed through the micro-channel, the chemicals contacting the chemically-modified substrate as they pass through the microchannels.

The PDMS master can be adhered to the chemically-modified substrate via surface tension, or via a clamp, frame, adhesive, or any other suitable means to bias the PDMS master against the chemically-modified surface.

As noted above, this same approach can also be used to make very complex microfluidic channel systems in PDMS. For example, Anderson et al. describe a procedure called the "membrane sandwich" method to fabricate 3-dimensional microfluidic channel systems. In this approach, a thin membrane having channel structures molded on each face (and with connections between the faces) is sandwiched between two thicker, flat slabs that provide structural support. Two masters are fabricated by rapid prototyping, as described above, using two-level photolithography and replica molding. The masters are aligned face to face, under pressure, with PDMS prepolymer between them. The PDMS is cured thermally. The masters have complementary alignment tracks so registration is straightforward. The resulting, thin PDMS membrane can be transferred and sealed to another membrane or slab of PDMS, without distorting the features within the PDMS masters. This approach can fabricate a membrane that contains a channel that crosses over and under itself, but does not intersect itself. Thus, this approach can generate topologically complex microfluidic systems.

Surface Plasmon Resonance (SPR)-Capable Substrates

As noted above, SPR is known. In the preferred embodiment of the present invention, the chemically-modified substrate is an SPR-capable substrate. In other words, the preferred chemically-modified substrate for use in the present invention is a substrate than can function as a substrate for acquiring SPR data or images.

In a preferred embodiment, a chemically-modified substrate is fabricated as described in U.S. Pat. No. 6,127,129, issued Oct. 3, 2000, to Corn et al. This protocol proceeds as follows:

(1) Self-assemble an co-modified alkanethiol monolayer on a metal substrate. The ω-modification to the alkanethiol may be the addition of any moiety that enables further covalent linkages to be made to the ω-terminus of the alkanethiol. Such modifications include, without limitation, the addition of an amine group, a hydroxyl group, a carboxyl group, or a thiol group to the co carbon of the alkanethiol chain. The alkanethiol monolayer is preferably an amino-$C_8$-$C_{24}$-alkanethiol, a straight-chain alkane being much preferred to branched alkane; the most preferred ω-modified alkanethiol is MUAM.

(2) React the ω-modified alkanethiol surface with a hydrophobic protecting group, most preferably Fmoc.

(3) Photopattern the surface to create an array of bare metal areas.

(4) Re-assemble using additional ω-modified alkanethiol to fill in the bare metal array elements, thereby yielding islands of ω-modified alkanethiol.

(5) Covalently attach biomolecules or cells to the islands of co-modified alkanethiol.

(6) Remove the protecting group from the array background.

(7) React the background with a material, preferably PEG, to make the background resistant to non-specific protein binding.

To ensure the quality of the finished product, each of the above steps may be monitored using PM-FTIRRAS, contact angle measurements, and scanning-angle SPR.

Each of these steps in now described in greater detail:

Step (1). In step (1), a monolayer of ω-modified alkanethiol, preferably an amine-terminated alkanethiol, most preferably MUAM, is self-assembled from an ethanolic solution onto a silanized substrate (glass or other substrate transparent to the wavelengths of radiation to be used in subsequent analysis, such as SPR) coated with a thin noble-metal film. In the preferred embodiment, a film of gold about 450 Å thick is used. The thickness of the metal film is not overly critical insofar as the film is uniformly applied and will function (in the preferred embodiment) in SPR imaging analysis. Self-assembled monolayers of ω-modified alkanethiols on gold have been described previously, see, for example, Thomas et al. (1995) J Am. Chem. Soc. 117:3830-3834, and are generally accepted by most to form well-ordered, monomolecular films. However, if left exposed for extended periods of time, the terminal amine groups of amino-modified alkanthiols will react with $CO_2$ to form carbamate salts on the surface. Consequently, amino-terminated alkanethiol-coated substrates should be handled with care and their exposure to $CO_2$ minimized.

Step (2). In step (2) of the array fabrication, the MUAM-covered surface is reacted with a reversible protecting group to create a hydrophobic surface. In the case of MUAM, an amine-modified alkanethiol, the protecting group is, appropriately, an amino-protecting group, preferably Fmoc. Fmoc is a bulky, hydrophobic, base labile, amine protecting group routinely used in the solid-phase synthesis of peptides. The choice of protecting group used is dependent in large measure upon the nature of the ω-modification made to the alkanethiol. If the ω-modification is the addition of a carboxyl group, a hydrophobic carboxy-protecting group would be used. Likewise, if the ω-modification is the addition of a hydroxyl or thiol group, a hydrophobic hydroxy- or thiol-protecting group, respectively, would be used. Any type of hydrophobic protecting group suitable for protecting the ω-modification used on the alkanethiol can be utilized in the present invention. Numerous such protecting groups, for any number of reactive moieties, such as amine, hydroxy, and carboxy functionalities, are known to the art. For example, chloride derivatives of both Fmoc and trityl to can be used to modify hydroxyl-terminated alkanethiols reversibly.

Step (3). In step (3), the bond anchoring the ω-modified alkanethiol to the metal substrate is selectively cleaved to yield a patterned surface of exposed metal. UV photo patterning is preferred to create the patterned surface, although the means to create the patterned surface is not critical so long as the method reliable yields the desired pattern. For example, microcontact printing methods can also be used to yield a patterned surface. The microfluidic channels described herein can also be used to create the patterns by flowing suitable reagents thought a set a microchannels of a desired geometric configuration to yield a pattern on the surface of the substrate. Using UV patterning, for example, the surface is exposed through a quartz mask to UV radiation which photo-oxidizes the gold-sulfur bond that anchors the alkanethiol monolayers to the surface. The surface is then rinsed, removing the photo-oxidized alkanethiol and leaving an array of bare metal pads surrounded by a hydrophobic MUAM+Fmoc background. Using photo patterning, features with dimensions as small as 50 mm have been achieved; using microcontact printing methods, arrays with features as small as about 100 nm are achievable.

Step (4). In step (4), the surface is again exposed to an ω-modified alkanethiol solution (in the preferred embodiment an ethanolic solution of MUAM) whereby the alkanethiol assembles into the bare gold regions producing a surface composed of hydrophilic MUAM pads surrounded by the hydrophobic Fmoc background. The difference in hydrophobicity between the reactive MUAM regions and the background is essential for the pinning of small volumes of aqueous biomolecule or cell solutions onto individual array locations.

Step (5). At step (5) in the process, biomolecules or cells (preferably nucleic acids) are then covalently attached to the surface. The MUAM reactive pads are first exposed to a solution of a bifunctional linker. The linker must be capable of binding at one end to the ω-modified alkanethiol surface and at the other end to the biomolecule or cell to be immobilized to form the desired array. Any bifunctional linker having these characteristics can be used in the present invention. The preferred bifunctional linker is SSMCC, a heterobifunctional linker which contains both an N-hydroxysulfosuccinimide (NHSS) ester and a maleimide functionality. The NHSS ester end of the molecule reacts with the free amine groups on an amino-modified surface, such as the MUAM spots, creating pads terminated in maleimide groups which are reactive toward thiols. Small volumes (0.08 to 0.1 L) of 1 mM solutions of 5'-thiol-modified DNA sequences are then spotted at discrete array locations and react to form a covalent attachment to the surface.

A variation on this attachment scheme wherein thiol-DNA is linked via SSMCC to a MUA/PL (11-mercaptoundecanoic acid/poly-L-lysine) bilayer has been used quite extensively, see U.S. Pat. No. 5,629,213. Other researchers have used the direct self-assembly of thiol-terminated DNA molecules on gold to prepare chemically-modified surfaces, but this method has the disadvantage that only weak forces exist for the self-assembly of oligonucleotide molecules and hence, the DNA can also non-specifically adsorb to the bare gold surface.

Here, a bifunctional linker is used to attach, for example, 5'-thiol-modified oligonucleotide sequences to reactive pads of aminoalkanethiol. The bifunctional linker preferably contains a functionality reactive toward amines and a functionality reactive toward aminoalkanethiols. The surface is first exposed to a solution of the linker, whereby one end of the molecule reacts with the aminoalkanethiol surface. Excess linker is rinsed away and the array surface is then spotted with 5'-thiol-modified nucleic acid which reacts with the other end of the bifunctional linker, thereby forming a covalent bond between the nucleic acid and the surface monolayer.

Step (6). In step 6, the protecting group, is removed from the array surface. Preferably, this is accomplished by exposure to a IM solution of the secondary amine, TAEA, in DMF. Many basic secondary amines can be used to remove Fmoc from the surface; for example, 1M solutions of ethanolamine and piperidine can be used with equal success. TAEA is a good choice as a deprotection agent because it effectively scavenges the dibenzofulvene byproduct and is efficiently rinsed from the array surface. After this deprotection step, the array background has been converted back to the original ω-modified alkanethiol surface.

Step (7). In the final step of the array fabrication, the ω-modified alkanethiol background is reacted with a compound to create a background that is resistant to the non-specific binding of proteins. The preferred compound for this purpose is PEG-NHS, although any compound which will selectively bind to the ω-modified alkanethiol surface and inhibit non-selective protein binding can be used. To monitor the binding of proteins to arrays of surface-bound biomolecules or cells, it is critical that the array background inhibit the non-specific adsorption of protein molecules. Significant amounts of such non-specific binding obscures the measurement of small amounts of protein binding at specific array locations.

Of course, in the present invention, all of the above steps, or any single step, or any combination thereof, may be completed by flowing chemicals through one or more of the microfluidic channels formed on the surface of the substrate.

EXAMPLES

The following Examples best illustrate the present invention. The Examples are included solely to provide a more complete understanding of the present invention. The Examples do not limit the scope of the invention disclosed and claimed herein in any fashion.

Standard Procedures

Gold substrates used in contact angle measurements were purchased commercially (Evaporated Metal Films) and those used in scanning or imaging SPR measurements were prepared by vapor deposition onto microscope slide covers that had been silanized with (3-mercaptopropyl)trimethoxysilane (Aldrich) in a manner similar to that reported by Goss et al. (1991) Anal. Chem. 63:85-88.

All oligonucleotides were synthesized on an ABI (Foster, Calif.) DNA synthesizer at the University of Wisconsin Biotechnology Center. Glen Research's (Sterling, Va.) "5'-Thiol-Modifier C6" and ABI's "6-FAM" were used for 5'-thiol-modified and 5'-fluorescein-modified oligonucleotides respectively, and "Spacer Phosphoramidite 18" (Glen Research) was used for the addition of an ethylene glycol spacer region. Thiol-modified oligonucleotides were deprotected as outlined by Glen Research's product literature. (Glen Research Corp. (1990) "User Guide to DNA Modification and Labeling"). Before use, each oligonucleotide was purified by reverse-phase binary gradient elution HPLC (Shimadzu (Columbia, Md.) "SCL-10AVP") and DNA concentrations were verified with an HP8452A UV-VIS spectrophotometer (Hewlett-Packard, Palo Alto, Calif.).

SPR Imaging Apparatus: The in situ SPR imaging instrument is a modified version of that described previously, (Jordan & Corn 1997; Thiel et al. 1997; Jordan et al. 1997; and Frutos et al. 1998), in which the HeNe laser and beam expander have been replaced by a collimated white light source/bandpass filter combination. A more thorough discussion of this modification in the context of near IR (NIR) SPR imaging is reported elsewhere, see Nelson et al. (1999). In short, a collimated, polychromatic beam of light was used to illuminate an SF10 prism/Au/thin film/buffer assembly at a fixed incident angle near the SPR angle. The reflected light was passed through a 10 nm bandpass filter (830 nm) and was collected with an inexpensive CCD camera. Differences in the reflected light intensity measured at various locations on the sample create the image and are a direct result of differences in the thickness or refractive index of the material bound at the gold surface.

Example 1

Demonstration of 1-Dimensional Array for Detection Nucleic Acids

Figure 1:
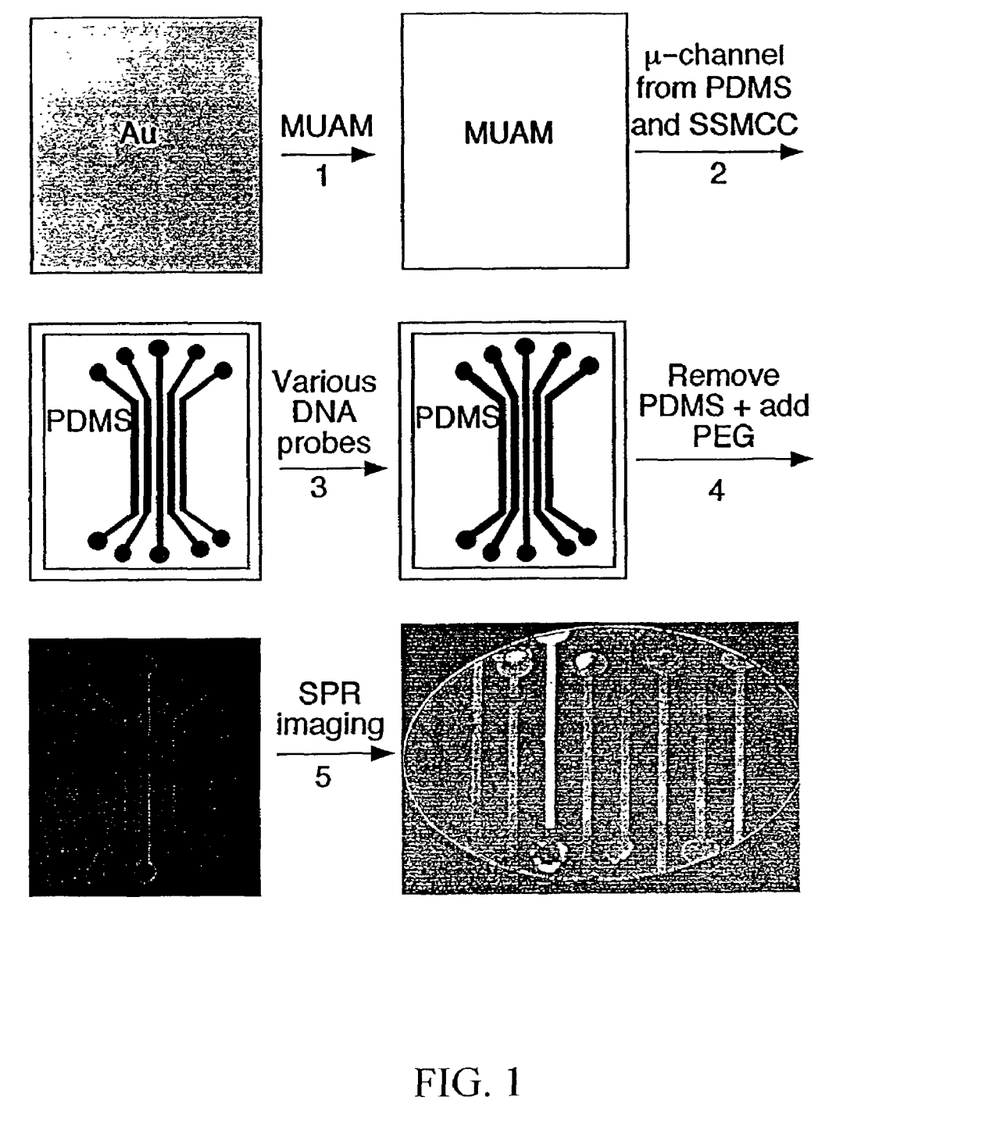
FIG. 1 is a schematic representation of the fabrication methodology used for creating 1-dimensional and 2-dimensional nucleic acid micro-arrays on a chemically-modified gold surface.

Referring now to FIG. 1, which shows the fabrication methodology according to the present invention for creating nucleic acid micro-arrays through the use of micro-fluidic channels in PDMS:

(1) A gold thin film surface is reacted with an amine-terminated alkanethiol (11-mercaptoundecylamine, MUAM) from a 1 mM ethanolic solution for two hours in order to form a self-assembled monolayer on the gold surface. (2) PDMS micro-channels were fabricated using the previously-described 1:1 photolithography technique of Anderson et al. (2000), and then attached to the MUAM-modified gold surface. A surface pattern is created by flowing a heterobifunctional linker, sulfosuccinimidyl 4-(N-maleimidomethyl)cyclohexane-1-carboxylate(SSMCC), through the PDMS micro-channels over the gold surface. The SSMCC reacts with the MUAM to create a maleimide-terminated alkanethiol monolayer. In order to overcome insufficient flow by capillary action, a simple differential pressure pumping system is used to deliver the reaction solutions.

(3) A variety of 5' thiol-modified single stranded DNA (ssDNA) probes are flowed into the PDMS micro-channels and then left to react with the maleimide-terminated gold surface for a least four hours. This creates a 1-dimensional DNA micro-array of different oligonucleotides on the surface.

(4) After cleaning the micro-channels with water, the PDMS is removed from the surface and the gold slide soaked in PEG-NHS (N-hydroxysuccinimidyl ester of methoxypoly (ethylene glycol) propionic acid MW 2000) solution in order to modify the MUAM background. This PEG-coated background is used to resist any non-specific adsorption during the hybridization experiments. An SPR image of the resulting surface is shown in the final panel of FIG. 1.

Figure 2:
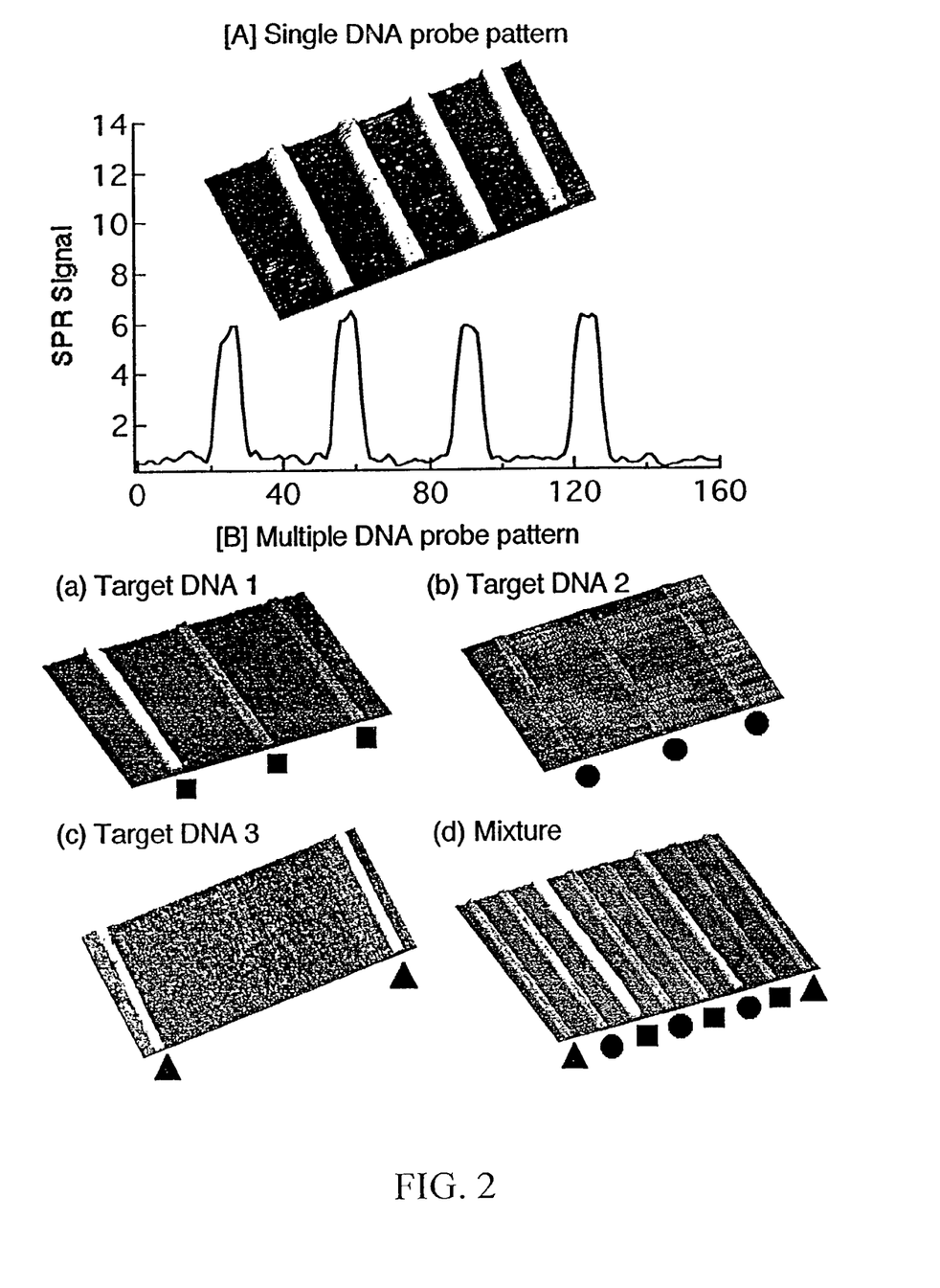

This array of attached ssDNA molecules can be used as a 1-dimensional array for the detection of DNA or RNA. FIGS. 2A and 2B are SPR difference images of the hybridization adsorption of complementary DNA onto 1-dimensional DNA arrays created by the process described herein. In FIG. 2A, the array lines are composed of the same 18-base ssDNA probe sequence. As can be seen in FIG. 2A, the same amount of complementary target ssDNA adsorbs to the different elements of the 1-dimensional array.

In FIG. 2B, three different 18-base pair ssDNA probes were used to create the array. When the array is exposed to individual complementary target DNA, only the correct array elements appear in the SPR image. Exposure of the surface to a mixture of all three complements lights up all of the array elements. These hybridization experiments were all performed on the same surface after removal of the previously hybridized target DNA by exposure to 8M urea. Differences in the amount of SPR response from each complementary target DNA are attributed to differences in ssDNA probe concentration during the array fabrication.

As shown by this example, the present method for creating 1-dimensional nucleic acid micro-arrays via micro-fluidics provides a simple strategy for creating such arrays. The subject method also has an advantage of being much simpler than the existing nucleic acid micro-array fabrication methodology based on photo patterning and reversible protection chemistry that has been described previously. This new methodology reduces the time required to make an array, and also reduces the amount of chemicals required in the fabrication process. The size of each individual array element is preferably approximately 50 μm in width, although larger or smaller elements can be used. In short, this method provides a simple way to place multiple probes on one array rapidly, easily, and with a minimum amount of reagents.

Example 2

Fabrication of 2-Dimensional DNA Micro-arrays Using Micro-channels

Figure 3:
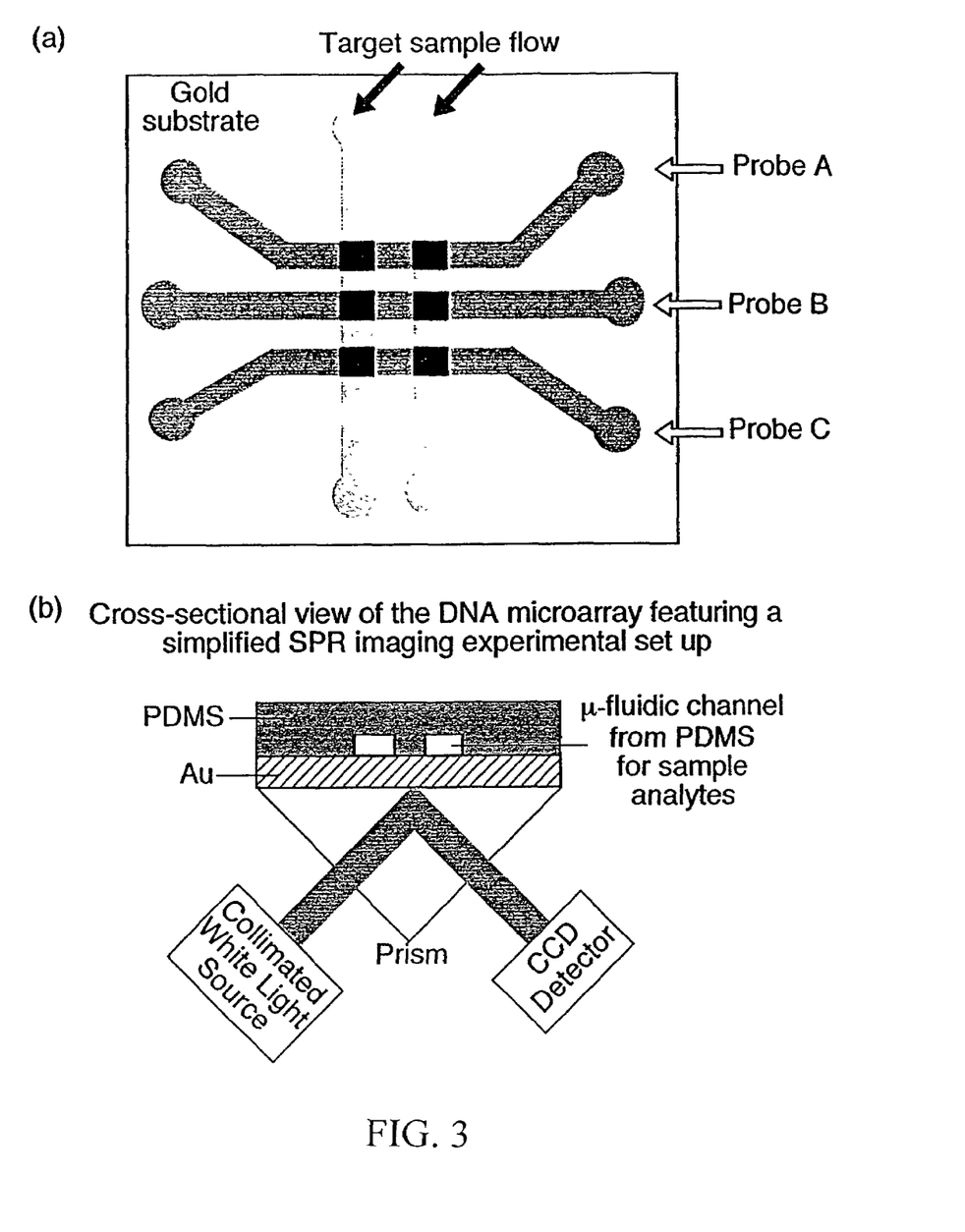
FIG. 3A is a schematic representation of a 2-dimensional nucleic acid micro-array used for SPR measurements.
FIG. 3B is a schematic representation of the SPR imaging experimental set-up incorporating micro-fluidics.

Referring now to FIG. 3A, in this example, the use of micro-fluidic channels has been extended to create 2-dimensional arrays based on the 1-dimensional DNA micro-arrays described in example 1. In these experiments, a 1-dimensional array as described in example 1 is first created on the gold surface. Then, a second set of PDMS micro-channels is attached to the surface so as to intersect the previously-deposited 1-dimensional array. This creates a 2-dimensional array of intersections that can be used to detect adsorption onto the surface-bound nucleic acids using either fluorescence microscopy or SPR imaging. Target solutions of complementary DNA or RNA are delivered via the second set of micro-channels so that the target solutions pass over the nucleic acids bound to the surface. The target solutions are allowed to contact the bound nucleic acids for a time sufficient to allow binding of the target to the bound probes. Analysis for binding can then proceed by SPR or fluorescent analysis, or both.

A schematic diagram of an SPR imaging apparatus is using the 2-dimensional approach described in this example is shown in FIG. 3B. Here, a nucleic acid array as described in example 1 is fabricated on the gold surface. (This array is not shown in FIG. 3B.) A PDMS micro-fluidics channel array is affixed on top of the first array such that the micro-channels intersect the elements of the nucleic acid array deposited on the gold surface. The remainder of FIG. 3B shows an abbreviated version of a standard SPR apparatus, including a prism, a light source, and a detector.

Note that throughout the examples, the arrays are shown as perpendicular channels. While this is the preferred geometry, the channels can be arranged in any desired geometry or pattern, without limitation. Thus, the individual array elements can be polygons of any size or number of sides (inscribed or circumscribed, interlocking, etc.), closed or opened curves, mono-disperse or of different sizes, shapes, and patterns. In short, the invention encompasses arrays of any geometric design or pattern. The micro-channels themselves may be of any cross-sectional geometry, without limitation (e.g., square, rectangular, circular, oval, triangular, etc.). The channels may be of consistent, regular geometry from end to end, or may change geometry or be of irregular geometry from end to end.

Example 3

SPR Imaging Using 2-Dimensional Arrays

Referring now to FIGS. 4A through 4D, these figures are SPR difference images of specific hybridization of complementary DNA onto a 2-dimensional DNA array. Each array element is 300 μm by 300 μm. Specific hybridization and adsorption of each probe was achieved without nonspecific adsorption or other interferences. Of particular note is that these DNA micro-arrays reduce the sample volume required for SPR analysis by an order of magnitude when compared to conventional flow cell system.

In this example, three different ssDNA probes were affixed to a gold surface in roughly parallel channels, one type of DNA per channel using the exact approach described in example 1. A PDMS micro-channel array having two parallel channels was then affixed on top of, and perpendicular to, the previously-deposited ssDNA probes, so that each channel intersected all three of the previously-deposited ssDNA probes. Complementary ssDNA was then flowed through the channels separately (FIGS. 4A, 4B, and 4C, respectively) and the all three complementary ssDNAs were flowed through each channel simultaneously (FIG. 4D).

Figure 4:
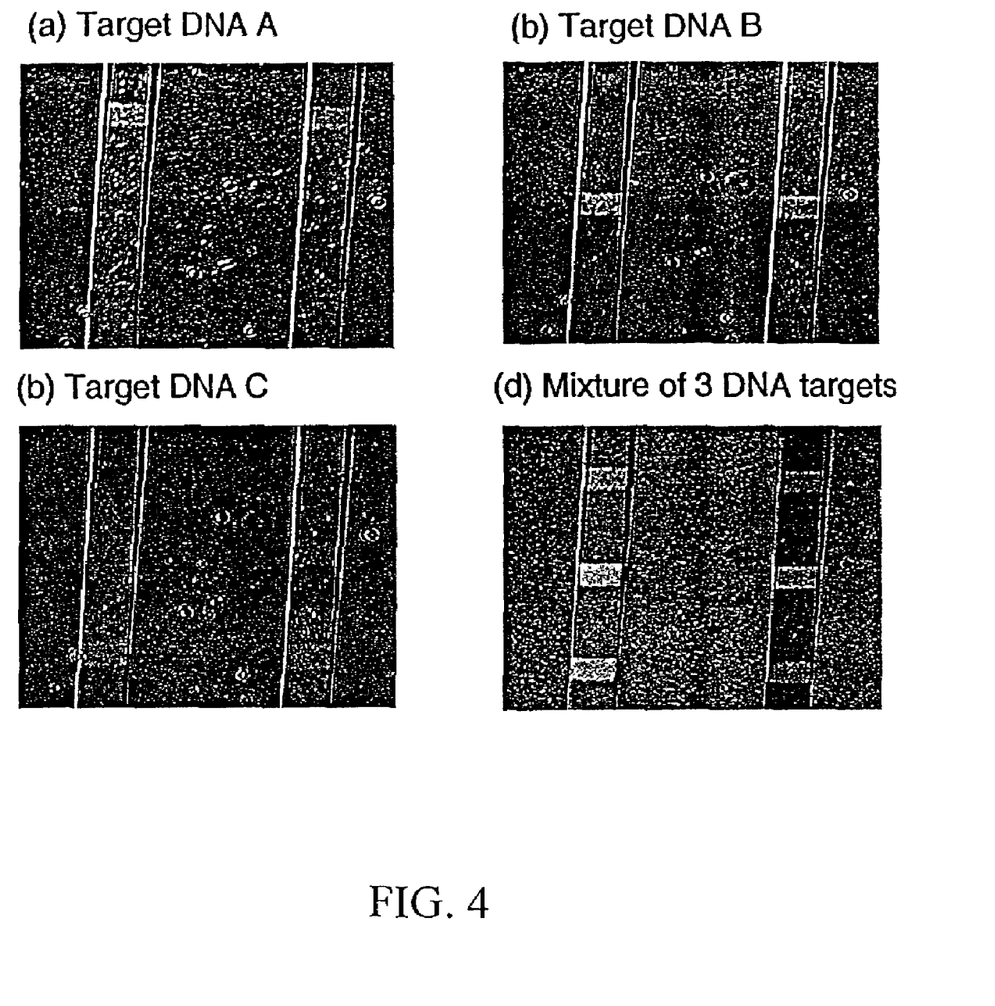
FIGS. 4A, 4B, 4C, and 4D are SPR difference images showing hybridization of target DNA onto a 2-dimensional micro-array of surface-bound probe DNA molecules. Hybridization onto the probe DNA array is indicated by a change in the percent reflectivity.

As shown in the figures, when an individual complementary ssDNA was passed through the micro-channels, the ssDNA bound only to its complementary mate, as shown in FIGS. 4A, 4B, and 4C, each of which show only one SPR image. When all three complementary ssDNAs were simultaneously passed through the micro-channels, three SPR images appear (FIG. 4D). This example illustrates that the 2-dimensional array described herein can be used to distinguish and analyze differential interactions of nucleic acids.

Example 4

SPR Imaging of In Vitro Transcribed GUS mRNA

Figure 5:
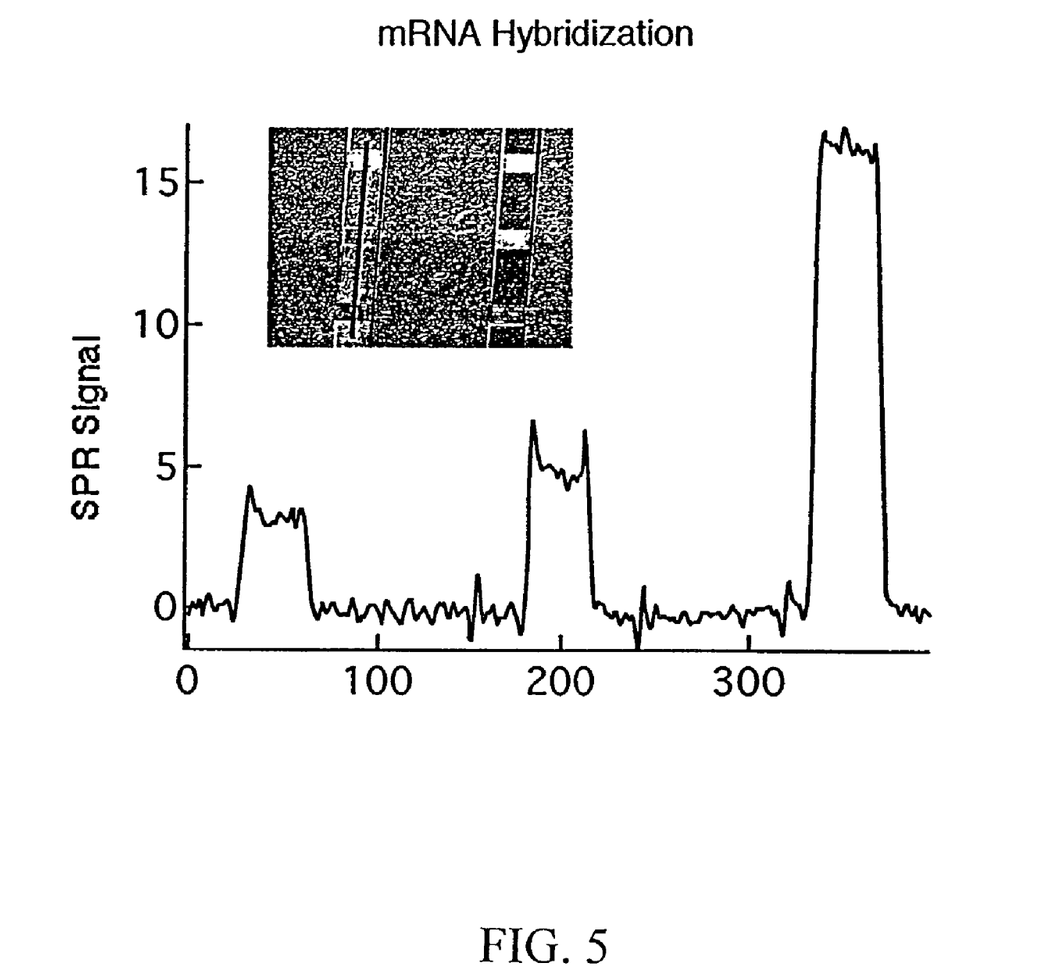
FIG. 5 is an SPR difference image and corresponding signal intensity graph showing hybridization of in vitro transcribed GUS m-RNA onto a 2-dimensional micro-array of surface-bound probe DNA. Hybridization onto the probe DNA array is indicated by a change in the percent reflectivity.

Referring now to FIG. 5, the 2-dimensional approach described in example 3 was used to detect in vitro transcribed GUS mRNA using SPR imaging. Here, cDNA sequences complementary to GUS PCR products were bound to the gold surface in three parallel array elements. A two-channel PDMS micro-array was affixed on top of, and perpendicular to the deposited DNA elements. GUS PCR products were then passed through the micro-channels for a time sufficient to allow hybridization to occur. The GUS PCR products, from *Arabadopsis*, were created and supplied by University of Wisconsin Plant Pathology Group. The results of the RNA hybridization experiment are shown in FIG. 5. Different signal strengths for the different probes are attributed to variations in RNA binding efficiency.

Example 5

Fluorescence Microscopy Using 2-Dimensional Arrays

Figure 6:
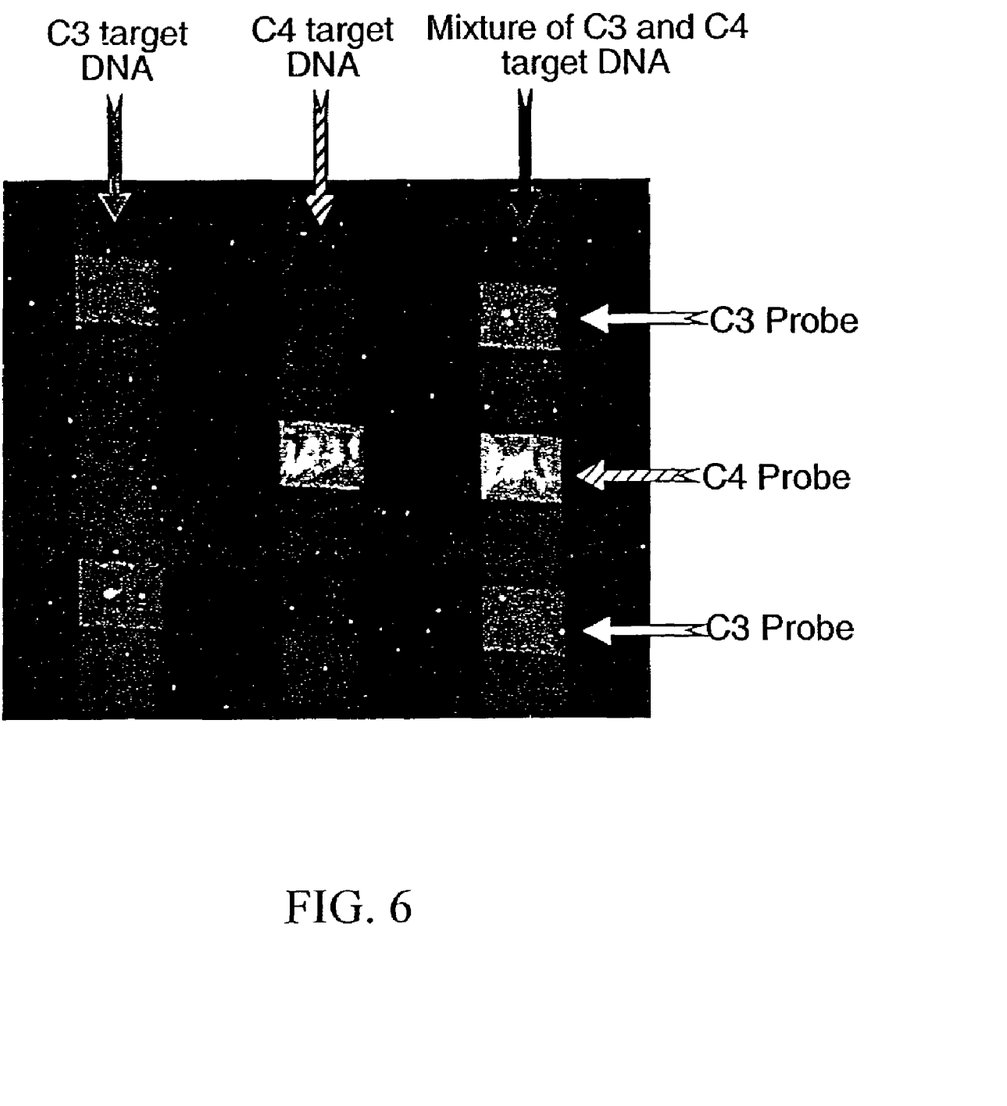
FIG. 6 is a fluorescence image of fluorescently-labeled target DNA hybridized onto an array of surface-bound probe DNA.

Referring now to FIG. 6, in this example, a 2-dimensional array of channels, each 75 μm in width was assembled as described in example 4. Here, however, the 2-dimensional array was analyzed by fluorescence microscopy. FIG. 6 is a fluorescence microscope image showing two different sequences of hybridized DNA using a perpendicular micro-channel 2-dimensional DNA array. A total of 2 μL of a 2 μM fluorescently-labeled complementary DNA was used for each channel. As can be seen in FIG. 6, specific hybridization of each DNA probe was obtained without any non-specific binding onto the background. Additionally, the 2-dimensional DNA array could be reused multiple times without any degradation of the signal.

This new methodology allows the rapid creation of 2-dimensional arrays for SPR imaging and fluorescence imaging of DNA-DNA, RNA-DNA and DNA-protein binding events. One of the major advantages of this technique is that it allows very small sample volumes to be analyzed by SPR. Previously, the relatively large amount of sample required for SPR analysis has been a problem—many experiments yield only a very small amount of nucleic acid for analysis.

For example, SPR imaging measurements using the micro-fluidic channels in FIG. 5 were used to detect GUS mRNA from a 2 μL sample that contained only 1 femtomole of mRNA. If smaller micro-wells are implemented, the solution volume can be reduced from 2 μL to 200 μL.

Additionally, the method described herein can be implemented on other substrates, for example, the same fabrication process can be applied to silicon, carbon, and germanium surfaces using the amine-termination chemistry of Strother et al. (2000a) and (2000b).

CITATIONS

Anderson et al. (2000) *Anal. Chem.* 72:3158-3164.
Brockman et al. (1999) *J. Am. Chem. Soc.* 121:8044-8051.
Brockman et al. (2000) *Ann. Rev. Phys. Chem.* 51:41:63.
Duffy et al. (1998) *Anal. Chem.* 70:4974-4984.
Effenhauser et al. (1997) *Anal. Chem.* 69:3451-3457.
Fodor (1997) *Science* 277:393-395.
Frutos et al. (1997) *Nucleic Acids Res.* 25:4748-4757.
Frutos et al (1998) *J. Am. Chem. Soc.* 120:10277-10282.
Frutos et al. (1998) *Anal. Chem.* 70:449A-455A.
Frutos et al. (2000) *Langmuir* 16:2192-2197.
Hickel et al. (1989) *Nature* 339:186.
Jo et al. (2000) *Microelectrochemical Systems* 9:76-81.
Jordan et al. (1997) *Anal. Chem.* 69:4939-4947.
Jordan & Corn 1997 *Anal. Chem.* 69(7):1449-1456.
Lockhart, et al. (1996) *Nature Biotechnology* 14:1675-1680.
Nelson et al. (1999) *Anal. Chem.* 71:3928-3934.
Nelson et al. (2001) *Anal. Chem.* 73:1-7.
Pease et al. (1994) *Proc. Natl. Acd. Sci. USA* 91:5022-5026.
Rothenhausler & Knoll (1988) *Nature* 332:615-617.
Silin & Plant (1997) *Trends in Biotechnol.* 15.
Strother et al. (2000a) *Nucleic Acids Research* 28:3535-3541.
Strother et al. (2000b) *J. Am. Chem. Soc.* 122:1205-1209.
Tarlov et al. (1993) *J. Am. Chem. Soc.* 115:5305-5306.
Thiel et al. (1997) *Anal. Chem.* 69:4948-4956.
Winzeler et al. (1998) *Science* 281:1194-1197.

What is claimed is:

1. A micro-fluidic, biomolecule micro-array on a chemically-modified substrate comprising:
    a chemically-modified substrate that is dimensioned and configured for surface plasmon resonance measurements having defined thereon an array of biomolecules covalently bonded to the chemically-modified substrate;
    a housing having disposed therein a plurality of non-intersecting micro-grooves in one plane, the housing adhered in face-to-face orientation to the chemically-modified substrate in such a fashion that the micro-grooves of the housing intersect the array of biomolecules, thereby defining a set of micro-channels through which can be passed reagents that will make contact with the array of biomolecules covalently bonded to the substrate.

2. The micro-array of claim 1, wherein the chemically-modified substrate is selected from the group consisting of chemically-modified gold, silver, platinum, copper, cadmium, aluminum, silicon, germanium, and carbon.

3. The micro-array of claim 1, wherein the chemically-modified substrate is chemically-modified gold or silicon.

4. The micro-array of claim 1, wherein the housing is polydimethylsiloxane.

5. A method of analyzing interactions between biomolecules comprising:

(a) providing a micro-fluidic, biomolecule micro-array on a chemically-modified substrate comprising:
    a chemically-modified substrate dimensioned and configured for surface plasmon resonance measurements having defined thereon an array of biomolecules covalently bonded to the chemically-modified substrate;
    a housing having disposed therein a plurality of non-intersecting micro-grooves in one plane, the housing reversibly attached in face-to-face orientation to the chemically-modified substrate in such a fashion that the micro-grooves of the housing intersect the array of biomolecules, thereby defining a set of micro-channels through which can be passed reagents that will make contact with the array of biomolecules covalently bonded to the substrate; and (b) passing through the micro-channels one or more solutions suspected of containing molecules capable of interacting with the array of biomolecules bound to the chemically-modified substrate; and then (c) analyzing the chemically-modified substrate of step (b) via surface plasmon resonance measurements to determine if any interaction has occurred.

6. A micro-fluidic, biomolecule micro-array on a chemically-modified substrate comprising:
    a chemically-modified substrate having defined thereon an array of biomolecules covalently bonded to the substrate, wherein the chemically-modified substrate is dimensioned and configured for surface plasmon resonance;
    a polydimethylsiloxane housing having disposed therein a plurality of non-intersecting micro-grooves in one plane, the polydimethylsiloxane housing adhered in face-to-face orientation to the chemically-modified substrate in such a fashion that the micro-grooves of the polydimethylsiloxane housing intersect the array of biomolecules, thereby defining a set of micro-channels through which can be passed reagents that will make contact with the array of biomolecules deposited on the substrate.

7. The micro-array of claim 6, wherein the chemically-modified substrate is selected from the group consisting of chemically-modified gold, silver, platinum, copper, cadmium, aluminum, and, germanium.

8. The micro-array of claim 6, wherein the chemically-modified substrate is chemically-modified gold.

9. The micro-array of claim 6, wherein the chemically-modified substrate is chemically-modified silicon or carbon.

10. A micro-fluidic, biomolecule micro-array on a chemically-modified substrate comprising:
    a chemically-modified gold substrate dimensioned and configured for surface plasmon resonance measurements having defined thereon an array of biomolecules covalently bonded to the substrate;
    a polydimethylsiloxane housing having disposed therein a plurality of non-intersecting micro-grooves in one plane, the polydimethylsiloxane housing adhered in face-to-face orientation to the chemically-modified substrate in such a fashion that the micro-grooves of the polydimethylsiloxane housing intersect the array of biomolecules, thereby defining a set of micro-channels through which can be passed reagents that will make contact with the array of biomolecules deposited on the substrate.

* * * * *